(12) United States Patent
Fojtik

(10) Patent No.: US 7,976,511 B2
(45) Date of Patent: *Jul. 12, 2011

(54) HAND-HELD ASPIRATION SYRINGE AND METHODS

(75) Inventor: Shawn P. Fojtik, Park City, UT (US)

(73) Assignee: Control Medical Technology, LLC, Park City, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/468,729

(22) Filed: May 19, 2009

(65) Prior Publication Data

US 2009/0227894 A1    Sep. 10, 2009

Related U.S. Application Data

(63) Continuation of application No. 11/431,420, filed on May 9, 2006, now Pat. No. 7,534,234.

(51) Int. Cl.
*A61M 5/315* (2006.01)

(52) U.S. Cl. ........ 604/223; 604/181; 604/187; 604/227; 604/228; 222/386

(58) Field of Classification Search .............. 604/223, 604/181, 187, 227, 228, 500, 224, 229, 232–235, 604/246, 183, 218; 222/391, 392, 386, 327
See application file for complete search history.

(56) References Cited

U.S. PATENT DOCUMENTS

| | | |
|---|---|---|
| 4,033,346 A | 7/1977 | Phillips et al. |
| 4,067,334 A | 1/1978 | Haller |
| 4,364,388 A | 12/1982 | Cech |
| 4,581,021 A | 4/1986 | Landau et al. |
| 4,632,669 A | 12/1986 | Phipps, Sr. et al. |
| 4,715,378 A | 12/1987 | Pope, Jr. et al. |
| 4,737,151 A | 4/1988 | Clement et al. |
| 4,832,692 A | 5/1989 | Box et al. |
| 4,968,303 A | 11/1990 | Clarke et al. |
| 5,288,285 A | 2/1994 | Carter |
| 5,304,147 A | 4/1994 | Johnson et al. |
| 5,306,147 A | 4/1994 | Dragan et al. |
| 5,330,074 A | 7/1994 | Wirsig et al. |
| 5,332,122 A | 7/1994 | Herold et al. |

(Continued)

OTHER PUBLICATIONS

21 C.F.R. § 870.1200, 1 pg, Apr. 1, 2003.

(Continued)

*Primary Examiner* — Kevin C Sirmons
*Assistant Examiner* — Laura C Schell
(74) *Attorney, Agent, or Firm* — Durham Jones & Pinegar

(57) ABSTRACT

A hand-held aspiration apparatus includes a handle configured for suspending and using the syringe with a single hand. The handle includes pivotally connected first and second members. The members of the handle may be pivotally connected at intermediate positions along the lengths thereof. The first member is associated with, and may be pivotally connected to, a syringe barrel, while the second member is associated with, and may be pivotally connected to, a syringe plunger. The members are configured and associated with one another in such a way that movement of portions thereof toward each other moves the plunger proximally through the barrel, which may create a vacuum in the barrel that may facilitate aspiration, and that movement of portions of the members away from one another moves the plunger distally through the barrel. The aspiration apparatus may be configured for a single-use (i.e., it may be disposable). Applications of use and methods of using a hand-held syringe are also disclosed.

21 Claims, 6 Drawing Sheets

U.S. PATENT DOCUMENTS

| | | |
|---|---|---|
| 5,336,201 A | 8/1994 | von der Decken |
| 5,439,131 A | 8/1995 | Kato |
| 5,507,727 A | 4/1996 | Crainich |
| 5,511,556 A | 4/1996 | DeSantis |
| 5,514,071 A | 5/1996 | Sielaff, Jr. et al. |
| 5,560,373 A | 10/1996 | De Santis |
| 5,569,208 A | 10/1996 | Woelpper et al. |
| 5,733,258 A | 3/1998 | Lane |
| 5,951,517 A | 9/1999 | Lampropoulos et al. |
| 5,968,017 A | 10/1999 | Lampropoulos et al. |
| 6,004,295 A | 12/1999 | Langer et al. |
| 6,024,728 A | 2/2000 | Schulz |
| 6,030,368 A | 2/2000 | Anwar et al. |
| 6,059,759 A | 5/2000 | Mottola et al. |
| 6,346,085 B1 * | 2/2002 | Schiffman .................... 600/565 |
| 7,534,234 B2 | 5/2009 | Fojtik |
| 2005/0085769 A1 | 4/2005 | MacMahon et al. |

OTHER PUBLICATIONS

21 C.F.R. § 870.1300, 1 pg, Apr. 1, 2002.
21 C.F.R. § 870.1650, 1 pg, Apr. 1, 2003.
21 C.F.R. § 880.5570, 1 pg, Apr. 1, 2003.
21 C.F.R. § 880.5860, 1 pg Apr. 1, 2002.
BD Products, BD (Becton Dickinson and Company) Product Information, 2003, 2 pgs.
Merit Medical Products, Merit Medical Products Information, 2002, 8 total pgs.
International Search Report for International Application No. PCT/US07/11270 mailed Jul. 21, 2008.

* cited by examiner

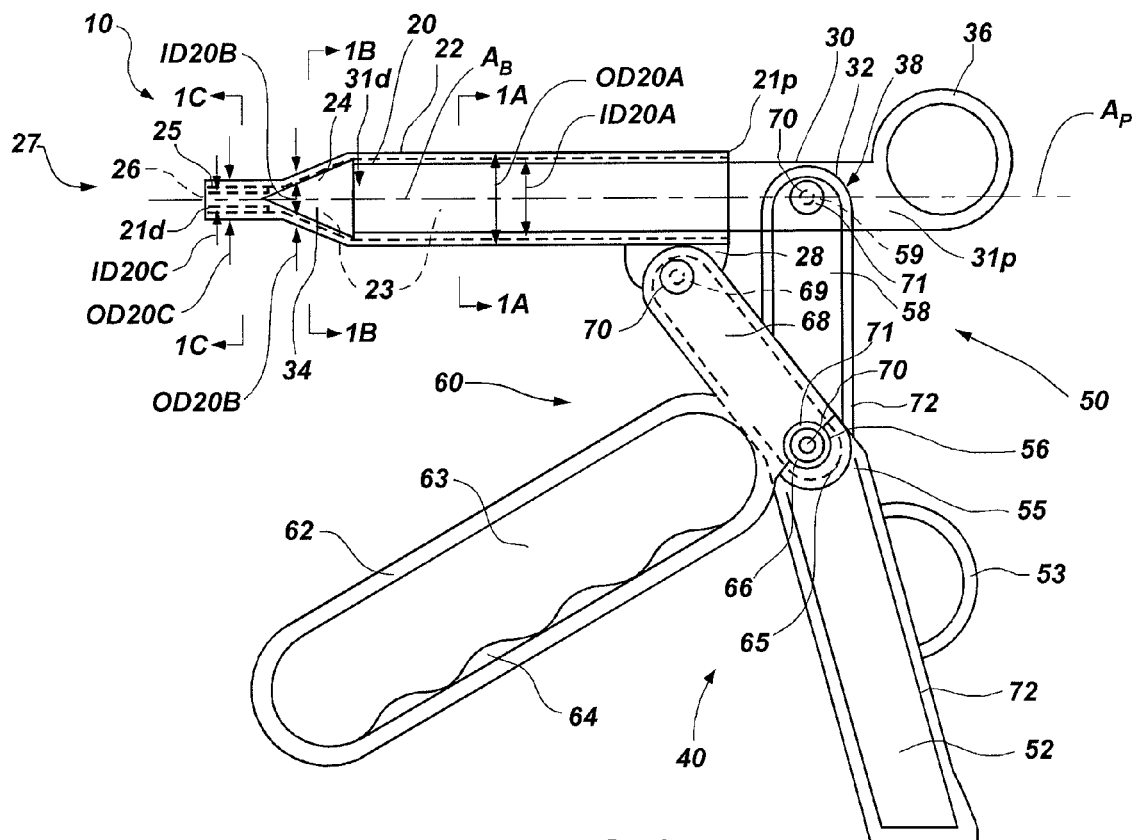
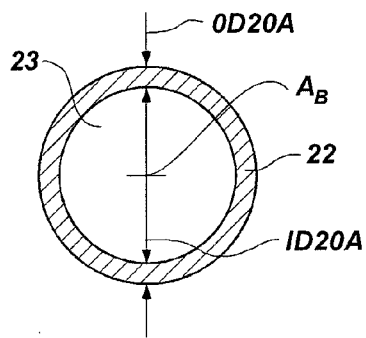
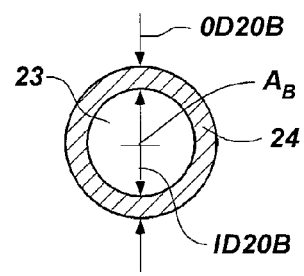
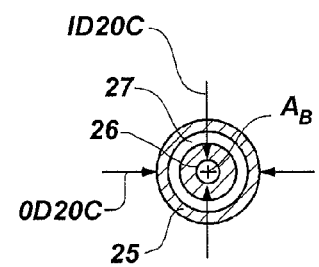
FIG. 1
FIG. 1A
FIG. 1B
FIG. 1C

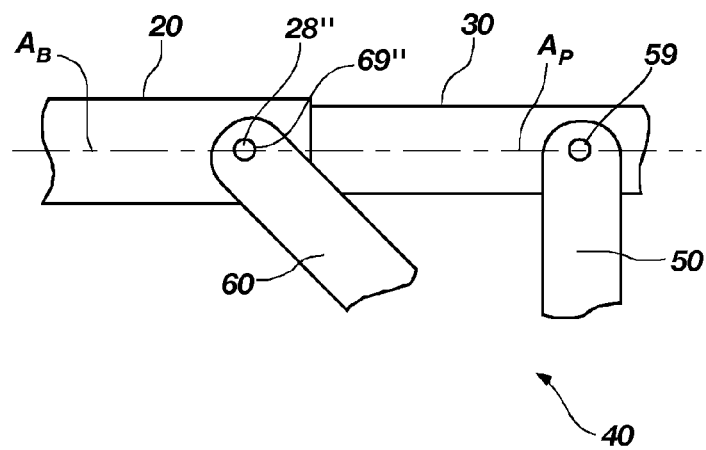
FIG. 1D
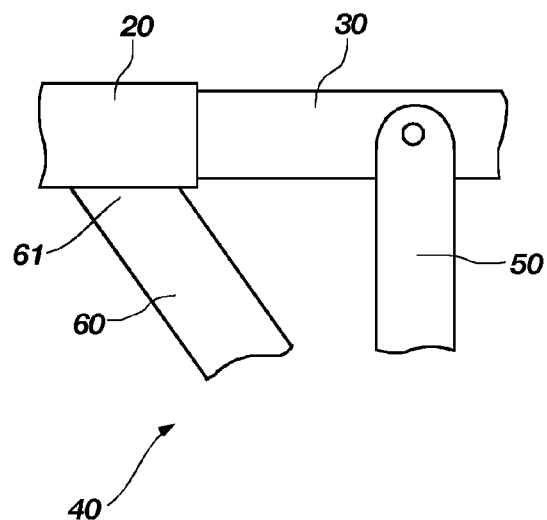 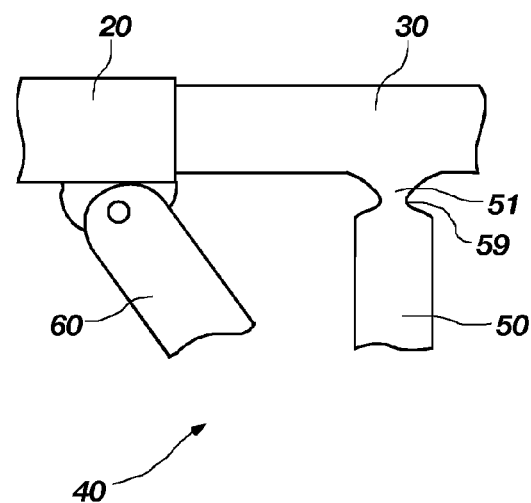
FIG. 6A      FIG. 6B

HAND-HELD ASPIRATION SYRINGE AND METHODS

CROSS-REFERENCE TO RELATED APPLICATION

This application is a continuation of application Ser. No. 11/431,420, filed May 9, 2006, which issued as U.S. Pat. No. 7,534,234 on May 19, 2009.

BACKGROUND OF THE INVENTION

1. Field of the Invention

The present invention relates generally to apparatus for facilitating the movement of a plunger of a syringe through a barrel of the syringe and, more particularly, to hand-held, hand operated apparatus that facilitate the movement of a plunger through a syringe barrel. More specifically, the present invention relates to hand-held apparatus with scissor grip type leveraged triggering systems that force a plunger of a syringe through the length of the barrel of the syringe.

2. Background of Related Art

The use of syringes for aspirating biological samples from the bodies of subjects is well known. Typically, the barrel of a syringe is placed in communication with a desired location of a subject's body, then a vacuum is created within the barrel of a syringe by pulling a plunger of the syringe toward a proximal end of the syringe (i.e., toward the syringe user, away from the body of the subject). When a vacuum is formed within the barrel of a syringe, fluid from the desired location is drawn into the syringe.

This process can be very difficult with existing devices, as syringes that are configured to reduce a user's exertion are also typically configured for fluid delivery rather than for aspiration. For example, in many conventionally configured syringes, aspiration is effected by holding the barrel of the syringe with one hand while pulling the plunger with another hand. Similar actions must be taken when many other types of manually operated devices are used to facilitate aspiration with a syringe.

There are needs for syringes that are configured to be held, or suspended, and operated by the same hand of a user and that may be comfortably operated.

SUMMARY OF THE INVENTION

The present invention includes aspiration apparatus.

By way of nonlimiting example, an aspiration apparatus according to the present invention may comprise a syringe. Such a syringe may include a handle that is configured to effectively reduce the amount of force that must be applied by a user to aspirate a sample from the body of a subject. Optionally, the handle may be configured so that aspiration is effected when members thereof are moved together.

An example of an aspiration apparatus of the present invention includes a hand-held, hand-operated syringe with a handle that is leveraged in such a manner as to apply more pressure to the plunger or barrel of the syringe than a user applies to the handle. The handle may include pivotally connected members, one of which is secured in relation to a barrel of a syringe, the other of which is secured in relation to a plunger of the syringe. The members of the handle are configured and oriented relative to one another in such a way as to facilitate holding (e.g., suspension), manipulation, and use of the aspiration apparatus with one hand. A first handle may be rigidly, flexibly, or pivotally associated with the syringe barrel, while the second handle may be rigidly, flexibly, or pivotally associated with the syringe plunger.

In an example of an embodiment of a handle that includes connection points, the handle may resemble scissors and includes two members, a first of which is configured to be held by the fingers of an individual and the second of which is configured to be held by the individual's thumb or positioned against the palm of the individual. The members are pivotally connected at intermediate, or somewhat central, locations along the lengths thereof. One or both of the first and second handle members may enable the user to grip both members with one hand while having a configuration (e.g., a shape, bend, etc.) that provides a user with a mechanical advantage while maximizing the amount of leverage provided as the handle members are forced toward one another. When the first and second members of the handle are moved toward or away from one another, the pivot point may remain in a substantially fixed position along the lengths of both the first and second members. Alternatively, the first pivot point may move in an elongate path relative to one or both of the first and second members of the handle as the positions of the first and second members are changed relative to one another. By way of example only, the first pivot point may move either eccentrically or in a linear fashion relative to one of the handle members as the positions of the members change while remaining substantially stationary relative to the other handle member.

In both reusable and single-use variations of an aspiration apparatus of the present invention, the aforementioned elements may be part of a single, integral syringe, or the handles may be configured for association with a separate, disposable syringe.

As an example of the use of an aspiration apparatus incorporating teachings of the present invention, a withdrawal element (e.g., a needle, catheter, etc.) that is in communication with a desired location of the body of a subject may be placed in communication with the receptacle of a barrel of the syringe. A sample may then be drawn through the withdrawal element and into the barrel by moving the first and second members of the handle toward one another. The barrel may then be removed from communication with the withdrawal element, and the sample expelled from the barrel by moving the members of the handle away from each other.

Other features and advantages of the present invention will become apparent to those of ordinary skill in the art through consideration of the ensuing description, the accompanying drawings, and the appended claims.

BRIEF DESCRIPTION OF THE DRAWINGS

In the drawings, which illustrate exemplary embodiments of aspiration apparatus incorporating teachings of the present invention and features thereof:

FIG. 1 is a side view of an aspiration apparatus, in this instance a syringe, incorporating teachings of the present invention, including a syringe barrel, a plunger that is longitudinally movable within a receptacle of the syringe barrel, and a scissor-grip handle that includes two members with three connection points, a first between a first member of the handle and the syringe barrel, a second between the second member of the handle and the plunger, and a third between the two handle members;

FIGS. 1A-1C are cross-sections taken along lines 1A-1A, 1B-1B, and 1C-1C, respectively, of FIG. 1;

FIG. 1D illustrates a variation on the manner in which a member of a handle of the syringe of FIG. 1 may be connected to the barrel of that syringe;

FIG. 6A depicts a syringe with a fixed connection between a barrel and its corresponding handle;

FIG. 6B illustrates a syringe with a fixed connection between a plunger and its corresponding handle;

DETAILED DESCRIPTION OF THE INVENTION

Figure 2:
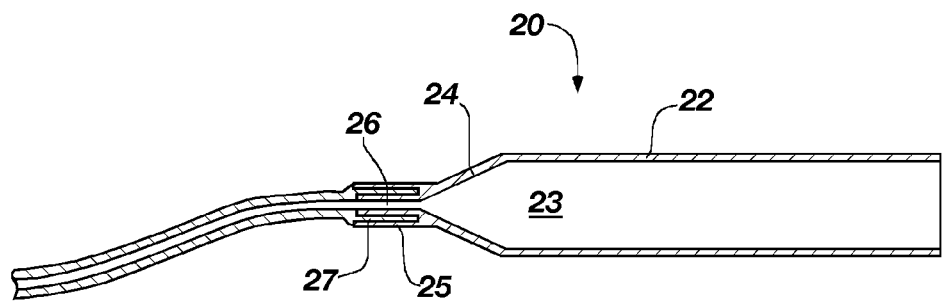
FIG. 2 is a cross-sectional representation of the syringe barrel of the syringe of FIG. 1, illustrating the syringe barrel in an assembled relationship with a catheter.

FIG. 1 illustrates an exemplary embodiment of an aspiration apparatus, here a syringe 10, incorporating teachings of the present invention. Syringe 10 includes a barrel 20, a plunger 30 associated with barrel 20, and a scissor-grip handle 40 which causes plunger 30 to move longitudinally relative to barrel 20. One or both of barrel 20 and plunger 30 may be removable from handle 40 to facilitate the replacement of these elements and the reuse of handle 40.

Barrel 20 of syringe 10 is an elongate member with a hollow interior extending through the length thereof. Along the majority of its length, barrel 20 is substantially uniform in both cross-sectional shape and cross-sectional dimensions. The region of barrel 20 having such substantial cross-sectional uniformity is referred to herein as a "body" 22. As depicted, body 22 extends from a proximal end 21p of barrel 20 to a tapered section or region 24 thereof. A syringe tip 25 is located on the opposite side of tapered section 24, at the distal end 21d of barrel 20.

As shown in FIGS. 1-1C the distances across opposed points of various cross-sections taken transverse to longitudinal axis $A_B$ of barrel 20 on the outer surface of barrel 20 or the outer diameter of barrel 20 are collectively referred to herein as "OD20." The corresponding distances across opposed points of various cross-sections taken transverse to longitudinal axis AB on the inner surface of barrel 20 or the inner diameter of barrel 20 are collectively referred to herein as "ID20."

As is depicted in FIGS. 1 and 1A, both OD20A and ID20A remain substantially the same along the substantial length of a body 22 of barrel 20. At tapered region 24, OD20 and ID20, which are respectively depicted at one location along the length of tapered region 24 as OD20B and ID20B, gradually (either linearly or along a curve) decrease from the sizes of OD20A and ID20A of body 22 to the much smaller sizes OD20C and ID20C of syringe tip 25. At syringe tip 25, the sizes of OD20C and ID20C are again substantially constant.

The taper of tapered region 24 may, in a specific embodiment, be oriented at an angle of about 15° to longitudinal axis $A_B$ of barrel 20. Other taper angles are, however, also within the scope of the present invention.

Turning now to FIG. 2, the hollow interior of barrel 20, within body 22 and tapered region 24 of barrel 20, forms a receptacle 23. The volume of receptacle 23 may correspond to a desired use for syringe 10 (FIG. 1). For example, in applications where only small volumes of materials will be aspirated or injected with syringe 10, barrel 20 may include a receptacle 23 with a relative small volume (e.g., 5 cubic centimeters ("cc"), 10 cc, etc.). When syringe 10 is to be used to aspirate or inject larger volumes of materials, the volume of receptacle 23 may also be larger (e.g., 20 cc, 30 cc, 60 cc, etc.). Alternatively, receptacle 23 of barrel 20 may have other standard syringe volumes or a volume that is tailored to a specific use for syringe 10.

The hollow interior of syringe tip 25 is referred to herein as a "lumen" 26. Lumen 26 may have a diameter of as small as about 1 mm (0.40 inch) or smaller. Of course, syringe tips 25 with different sizes of lumens 26 are within the scope of the present invention, as the size of a lumen 26 depends at least partially upon the gauge of a needle or the lumen size of a catheter to be coupled with syringe tip 25.

In addition, in order to facilitate the coupling of a needle or catheter with syringe tip 25, syringe tip 25 includes a coupling member 27 at or near the distal end 21D of barrel 20. Although FIG. 1 depicts coupling member 27 (see also FIG. 1C) as including a cylindrically shaped recess that extends partially into syringe tip 25, coupling members of other configurations, including, without limitation, threaded or non-threaded coupling features that facilitate the coupling of a needle, catheter, or other member to an outer surface of syringe tip 25, are also within the scope of the present invention.

Figure 3:
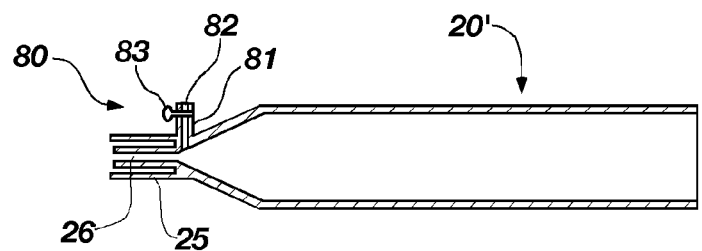
FIG. 3 is a cross-sectional representation of a variation of the syringe barrel illustrated in FIGS. 1 and 2, which includes an aspiration port that may communicate with a source or reservoir for introducing fluid into the syringe barrel upon appropriate movement of the plunger to increase the available volume within the syringe barrel.

As illustrated in FIG. 3, a variation of barrel 20' may include an aspiration port 80 proximate syringe tip 25. Aspiration port 80 facilitates the introduction of a fluid, such as a saline solution, medicine, anesthetic, indicator solution (e.g., dye, radioactive solution, radio-opaque solution or x-ray contrast media, etc.), other chemical compound, or the like from an external source into receptacle 23 of barrel 20. Aspiration port 80 is depicted as comprising a cylindrical protrusion 81, which is configured to have a length of tubing coupled thereto, and a lumen 82 that extends through protrusion 81 and communicates with lumen 26 of syringe tip 25. In addition, aspiration port 80 may include a valve 83, such as a stop cock type valve, which opens and closes lumen 82. Of course, other configurations of aspiration ports are also within the scope of the present invention.

Referring again to FIG. 1, barrel 20 also includes a handle connection element 28. As depicted, handle connection element 28 extends from body 22 at proximal end 21p of barrel 20 and includes an aperture formed therethrough. The aperture is sized and configured to receive a hinge element 70 and, thus, to facilitate the connection of a member of handle 40 to barrel 20.

Alternatively, as shown in FIG. 1D, a handle connection element 28" may include features on opposite sides of barrel 20. Such a connection point arrangement places the pivotal points that are established by connection elements 59 and 69" that are associated with handle 40 and second and first members 50 and 60, respectively, substantially in-line with axes $A_B$ of barrel 20 and $A_p$ of plunger 30.

While FIG. 1 depicts barrel 20, receptacle 23, and lumen 26 as having substantially cylindrical shapes with circular cross-sections taken transverse to a longitudinal axis $A_B$ of barrel 20, syringe barrels with any other suitable cross-sectional shapes (e.g., ovals, ellipses, polygons, etc.) are also within the scope of the present invention.

With continued reference to FIG. 1, plunger 30 is an elongate member with dimensions that permit plunger 30 to be inserted into receptacle 23 of barrel 20 through proximal end 21*p* thereof. Plunger 30 includes a body 32 and a head 34 at the distal end 31*d* of body 32. The proximal end 31*p* of body 32 and, thus, of plunger 30 is configured to have force applied thereto to facilitate movement of plunger 30 in both directions along a longitudinal axis $A_p$ of plunger 30.

Head 34 of plunger 30 may comprise a somewhat deformable, resilient member. By way of example, head 34 may be formed from silicone or any other resilient polymer (i.e., rubber) that is suitable for use in medical applications. The shape of head 34 may be substantially complementary to a shape of the portion of receptacle 23 of barrel 20 that is located within tapered region 24 and a portion of body 22 adjacent thereto. The size of head 34 may be substantially the same as or somewhat larger than the correspondingly shaped portion of receptacle 23 so as to facilitate the substantial displacement of fluid from receptacle 23 as plunger 30 is fully inserted therein.

In order to facilitate movement of head 34 of plunger 30 along the fill length of receptacle 23, the length of plunger 30 may be greater than the combined lengths of body 22 and tapered region 24 of barrel 20. Of course, in order to apply the amount of force necessary to move plunger 30 through the length of receptacle 23, body 32 of plunger 30 is may be formed from a more rigid material than that of head 34. Accordingly, head 34 may include a receptacle (not shown) that is configured to receive a corresponding head connection protrusion (not shown) at the distal end of body 32, as known in the art.

Proximal end 31*p* of plunger 30 includes a handle connection element 38. Handle connection element 38 includes an aperture formed through body 32 of plunger 30 at a location that facilitates the pivotal connection of a member of handle 40 thereto by way of a hinge element 70.

In addition, proximal end 31*p* of plunger 30 may include a secondary movement element 36, such as a loop or another member by which an individual may cause plunger 30 to move in one or both directions along longitudinal axis $A_p$ thereof.

Still referring to FIG. 1, handle 40 includes two elongate members, a first member 60 and a second member 50. First member 60 and second member 50 are pivotally connected with one another in a manner that, along with the shapes of first and second members 60 and 50, provides leverage, or a mechanical advantage, so as to decrease the amount of force that must be exerted by a user's hand to move plunger 30 relative to barrel 20.

First member 60, which is configured to be held with a user's fingers, includes a gripping end 62 and a barrel attachment end 68. In addition, first member 60 includes pivotal connection element 66 positioned at a central region 65 thereof, which is located substantially centrally along the length thereof, to facilitate connection of first member 60 to second member 50 of handle 40. Pivotal connection element 66 includes an aperture that has a circular shape and that receives a hinge element 70, or pivot pin, which, in turn, connects first member 60 and second member 50 to one another.

As shown, first member 60 includes an elongated loop 63 along gripping end 62, through which an individual's fingers may be inserted. Alternatively, or in addition to loop 63, gripping end 62 may include a finger grip 64 that is contoured so as to comfortably receive the fingers of a user.

Barrel attachment end 68 includes (e.g., terminates at) a barrel connection element 69 that facilitates the pivotal connection of second member 60 to the corresponding handle connection element 28 of barrel 20. As depicted, barrel connection element 69 comprises an aperture that is configured to receive a hinge element 70. Second member 60 and barrel 20 are pivotally connected to one another by properly positioning barrel attachment end 68 and handle connection element 28 against one another, with the apertures thereof in alignment, and inserting a single hinge element 70 through both barrel connection element 69 and handle connection element 28. Hinge element 70 may include an enlarged head 71 at each end thereof to maintain the assembled, pivotal relationship of barrel 20 and second member 60. Of course, other known types of pivotal connection arrangements between barrel 20 and second member 60 and their corresponding elements are also within the scope of the present invention.

First member 60 is bent, or angled, at some point along the length thereof, between gripping end 62 and plunger attachment end 68, to at least partially provide the desired amount of leverage for forcing plunger 30 to move longitudinally through (e.g., out of) receptacle 23 of barrel 20. As shown in FIG. 1, first member 60 is angled at central region 65 so that gripping end 62 thereof extends away from second member 50. Although FIG. 1 depicts gripping end 62 and plunger attachment end 68 as being oriented at an angle of about 90° relative to one another, other angles and bend locations are also within the scope of the present invention.

Still referring to FIG. 1, second member 50 of handle 40 is an elongate member that is configured to be held by a subject's palm or thumb. Second member 50 includes a gripping end 52 and plunger attachment end 58, as well as a central region 55 located between gripping end 52 and plunger attachment end 58.

Gripping end 52 of first member 50 may include a thumb loop 53 through which the thumb of a user of syringe 10 may be inserted.

Central region 55 of second member 50 includes a pivotal connection element 56 that corresponds to pivotal connection element 66 of first member 60. Pivotal connection element 56 may comprise an aperture formed through central region 55 and configured to receive hinge element 70. Upon properly orienting first member 60 and second member 50 relative to one another in an assembled relationship thereof and aligning the aperture of first member 60 with the aperture of second member 50, hinge element 70 may be inserted through the apertures to pivotally connect first and second members 60 and 50 to one another. Hinge element 70 may include an enlarged head 71 at each end thereof to maintain the assembled, pivotal relationship of first member 60 and second member 50.

Figure 4:
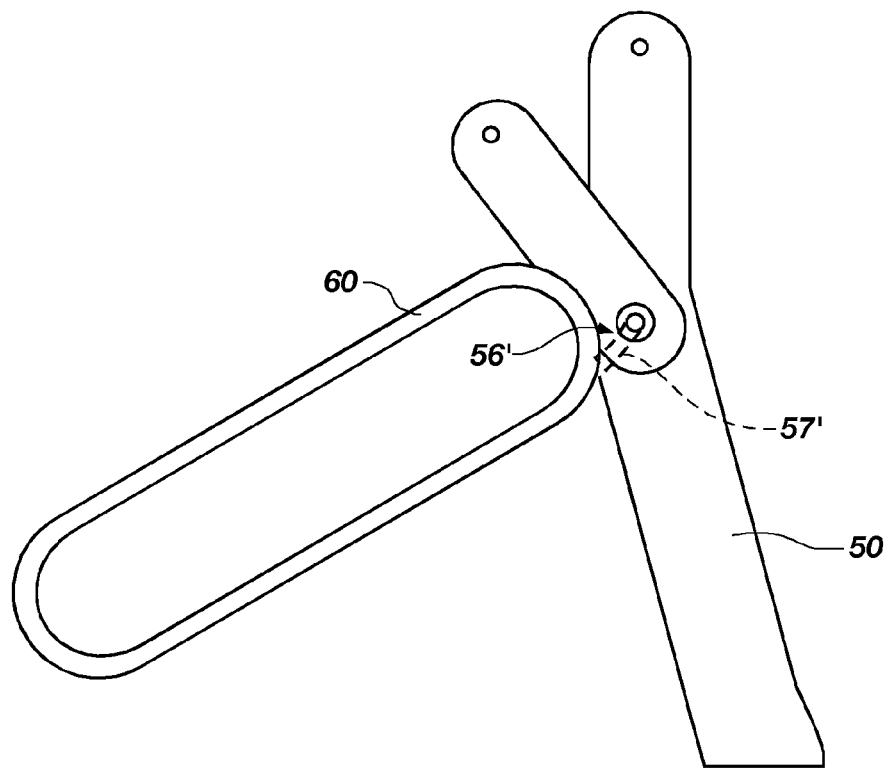
FIG. 4 is a side view that depicts a variation of the handle of FIG. 1, with one of the first and second members including an arcuate slot through which a movable connection member on the other of the two members moves when the handle members are moved relative to one another.

Alternatively, as depicted in FIG. 4, a variation of pivotal connection element 56' may comprise an arcuate slot 57', along the length of which pivotal connection element 56' may move as first and second members 60 and 50 are moved toward or apart from one another.

Figure 5:
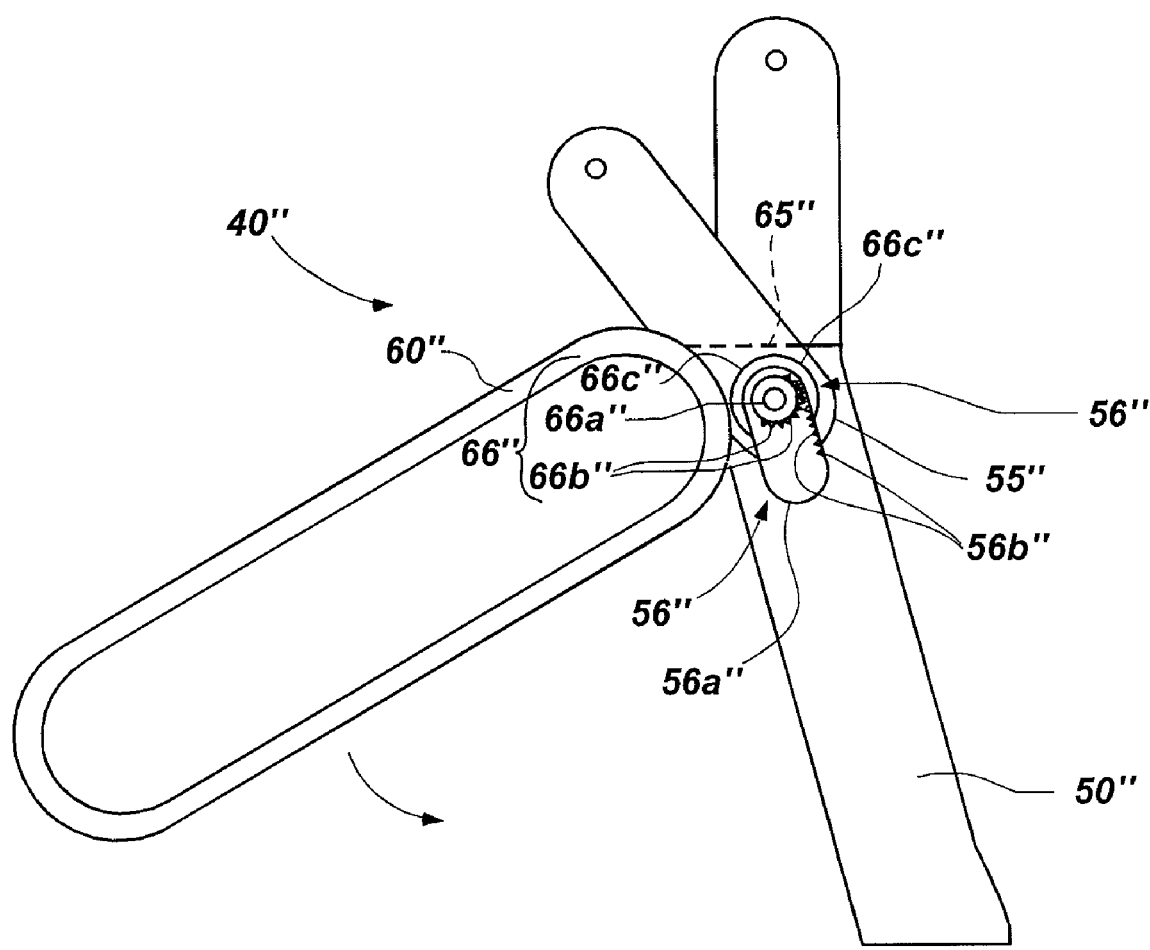
FIG. 5 is a side view that depicts another variation of the handle of FIG. 1, wherein one of the first and second handle members includes a partial gear member and the other of the first and second handle members includes an elongated slot with teeth along an edge thereof for receiving teeth of the partial gear member upon movement of the two handle members relative to one another.

As another alternative, shown in FIG. 5, a handle 40" of a syringe according to the present invention includes another embodiment of connection element 66" on central region 65"

of first member 60" and another, corresponding embodiment of pivotal connection element 56" on central region 55" of second member 50". Connection element 66", which protrudes from central region 65" and is fixed in relation thereto, includes a cylindrical section 66a", a series of adjacent teeth 66b" protruding from at least a portion of the curved surface of cylindrical section 66a", and an enlarged retention head 66c" adjacent cylindrical section 66a", opposite from the remainder of first member 60". The distance that cylindrical section 66a" protrudes from central region 65" of first member 60" may be slightly larger than the thickness of second member 50".

The corresponding pivotal connection element 56" of second member 50" comprises an elongated slot 56a" with a series of adjacent teeth 56b" protruding from at least a portion of an edge along the length of slot 56a". Teeth 56b" are configured and positioned complementarily to teeth 66b" of pivotal connection element 66" such that teeth 56b" and teeth 66b" cooperate by mutually engaging each other upon rotation of cylindrical section 66a" relative to slot 56a". The width of slot 56a" may be slightly larger than the diameter of cylindrical section 66a" of pivotal connection element 66" so as to substantially prevent side-to-side movement of pivotal connection element 66" relative to pivotal connection element 56". Consequently, the relative movement of pivotal connection elements 56" and 66" with respect to one another is substantially confined on the direction in which pivotal connection element 56" extends, which, as illustrated, is along the length of second member 50". Thus, when first and second members 60" and 50" are forced toward one another, pivotal connection element 66" rotates relative to pivotal connection element 56" and moves downward through slot 56a" of pivotal connection element 56". Conversely, when first and second handle members 60" and 50" are forced apart from one another, pivotal connection element 66" rotates and moves in the opposite direction relative to pivotal connection element 56".

Referring again to FIG. 1, handle 40 may additionally include a resilient element (e.g., a spring) may be associated with first and second members 60 and 50 (e.g., at or near hinge element 70) in such a way as to force first and second members 60 and 50 apart from one another when they are not being held together.

When first and second members 60 and 50, or variations thereof, have been properly assembled with one another, an adult user may be able to properly position their fingers on gripping end 62 and their thumb or palm against gripping end 52 while gripping ends 62 and 52 are spaced a maximum distance apart from one another with head 34 of plunger 30 located at distal end 21d of barrel 20.

Plunger attachment end 58 includes (e.g., terminates at) a plunger connection element 59 that facilitates the pivotal connection of first member 50 to the corresponding handle connection element 38 of plunger 30. Plunger connection element 59 may comprise an aperture that is configured to receive hinge element 70. First member 50 and plunger 30 are pivotally connected to one another by positioning plunger attachment end 58 against the appropriate location of plunger 30 with plunger connection element 59 and aperture (not shown) of handle connection element 38 in alignment. A single hinge element 70 is then inserted through both plunger connection element 59 and the aperture of handle connection element 38. Hinge element 70 may include an enlarged head 71 at each end thereof to maintain the assembled, pivotal relationship of plunger 30 and first member 50. Of course, other known types of pivotal connection arrangements between plunger 30 and first member 50 and their corresponding elements are also within the scope of the present invention.

Second member 50 of handle 40 may be bent, or angled, to increase the leverage provided by first member 60 and the scissor-like arrangement of first member 60 and second member 50. As illustrated, second member 50 is bent at central region 55 thereof so that gripping end 52 of second member 50 extends away from first member 60. This configuration and arrangement provides further leverage, or mechanical advantage, when drawing plunger 30 proximally (i.e., out of) barrel 20.

Of course one or both of first member 60 and second member 50 may include reinforcement ribs 72 or other reinforcement structures along at least a portion of the length thereof. As depicted, reinforcement ribs 72 are positioned along the edges of first member 60 and second member 50. Reinforcement ribs 72 may be positioned to prevent side-to-side bending of first member 60 or second member 50 during use of handle 40 to move plunger 30 relative to barrel 20.

FIGS. 6A and 6B illustrate variations of syringe 10 (FIG. 1), in which first member 60 and second member 50 of handle 40 are pivotally connected to one another, but at least one connection point between an end of a member 60, 50 of handle 40 and barrel 20 or plunger 30 does not pivot. In FIG. 6A, a connection point 61 between an end of second member 60 and barrel 20 does not pivot. In FIG. 6B, a connection point 51 between an end of first member 50 and plunger 30 does not pivot. While connection points 61 and 51 do not pivot, the ends of second and first members 60 and 50 may still be nonrigidly (e.g., flexibly) connected with barrel 20 and plunger 30, respectively (e.g., by way of a flexible connecting material, an integral region of reduced thickness, etc.). Alternatively, at least one connection point 61, 51 may be substantially rigid. Although FIGS. 6A and 6B illustrate only a single non-pivoting connection point 61, 51, a syringe may include two non-pivoting connection points 61, 51.

Figure 7:
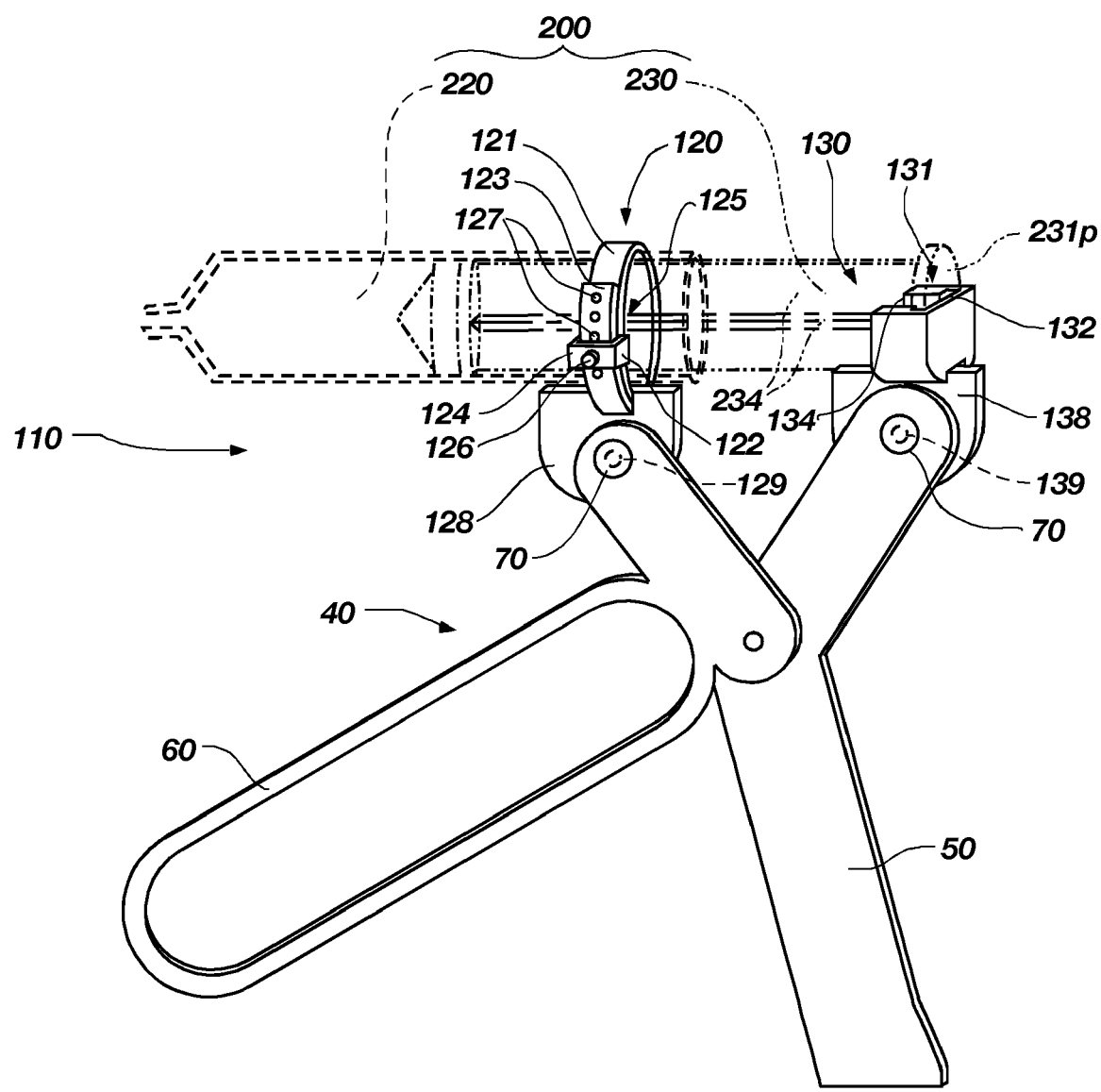
FIG. 7 is a side view of another embodiment of syringe incorporating teachings of the present invention, wherein a disposable syringe barrel and plunger may be assembled and used with a reusable handle.

Turning to FIG. 7, another embodiment of a syringe 110 according to the present invention is illustrated. Syringe 110 includes a scissor-grip handle 40, a barrel retaining member 120 pivotally secured to a first member 60 of handle 40, and a plunger biasing member 130 pivotally secured to a second member 50 of handle 40.

Barrel retaining member 120 is configured to engage and retain at least a portion of the barrel 220 of a syringe 200. The depicted, exemplary embodiment of barrel retaining member 120 includes a flexible, elongate member 121 with a receptacle 124 at one end 122 thereof. Receptacle 124 is configured to receive the other end 123 of elongate member 121, as well as to facilitate the movement of a received portion of elongate member 121 therethrough. When receiving end 123 of elongate member 121 has been inserted into or through receptacle 124, barrel retaining member 120 takes on an annular configuration, forming a barrel receptacle 125 that may receive a portion of barrel 220 of syringe 200. As elongate member 121 moves through receptacle 124, the size of barrel receptacle 125 changes. The position of a portion of elongate member 121 extending through receptacle 124 may be maintained by way of a size adjustment member 126 (e.g., a screw, a spring-biased pin, etc.) that protrudes into receptacle 124 to engage the portion of elongate member 121 therein. Elongate member 121 may also include retention recesses 127 (e.g., grooves, slots, etc.) that are oriented along the length of elongate member 121 and that are configured to receive an interior end of size adjustment member 126 so as to further maintain the position of elongate member 121 relative to receptacle 124 and, thus, the size of barrel receptacle 125.

Barrel retaining member 120 also includes a handle connection element 128 which extends from elongate member 121 and includes an aperture 129 therethrough. Aperture 129 is sized and configured to receive a hinge element 70 and, thus, to facilitate connection of a member of handle 40 to barrel retaining member 120.

Of course, other embodiments of barrel retaining members, which may be configured to receive a variety of different sizes of syringes or single syringe sizes, are also within the scope of the present invention.

With continued reference to FIG. 7, an exemplary embodiment of plunger biasing member 130 is configured to receive, retain, and apply force to a proximal end 231p of a plunger 230 of syringe 200. Accordingly, the illustrated plunger biasing retaining member 130 includes a plunger receiving portion 131 that is configured to receive and apply pressure to proximal end 231p of plunger 230. As illustrated, plunger receiving portion 131 includes a receptacle 132 that is configured to receive at least a portion of the disk-shaped proximal end 231p of a conventionally configured syringe plunger 230. In addition, plunger biasing retaining member 130 includes a slot 134 that is continuous with receptacle 132 and that is positioned and sized to receive a portion of at least one of the support ribs 234 of a conventionally configured syringe plunger 230. As depicted, proximal end 231p is substantially completely received within receptacle 132. Accordingly, slot 134 may include a narrow bottom section that receives a single, vertically oriented support rib 234 and a wider top section that receives opposed, horizontally oriented support ribs 234.

A handle connection element 138 is positioned adjacent to (beneath) plunger receiving portion 131 and includes an aperture 139 that is configured to receive a portion of a hinge element 70 and to pivotally connect plunger biasing member 130 to first member 50 of handle 40.

Handle 40 of syringe 110 may be configured as described previously herein.

While the various elements of a syringe according to the present invention (e.g., syringe 10) may be manufactured from any suitable material or materials, in some embodiments, each of the elements of the syringe may be formed by injection molding processes so as to afford low manufacturing cost and, consequently, to facilitate single-use, or disposability, of the syringe. For the more rigid elements, which, in syringe 10 (FIG. 1) include substantially all of the elements thereof with the exception of head 34 of plunger 30, polycarbonates, such as LEXAN®, manufactured by General Electric, or MAKROLON®, manufactured by Miles Chemicals, may be used. Of course, other medical grade plastics having properties (strength, rigidity, structural integrity, ability to be adequately sterilized while maintaining other desired properties, etc.) that are suitable for the desired functions of the various elements of a syringe may be used to form those elements. Alternatively, suitable metals, such as stainless steel, which have the desired properties may be used to form one or more of the elements of a syringe that incorporates teachings of the present invention. These configurations are not, however, requirements, nor are the materials or method of fabrication critical to any inventive aspect disclosed herein.

Figure 8A:
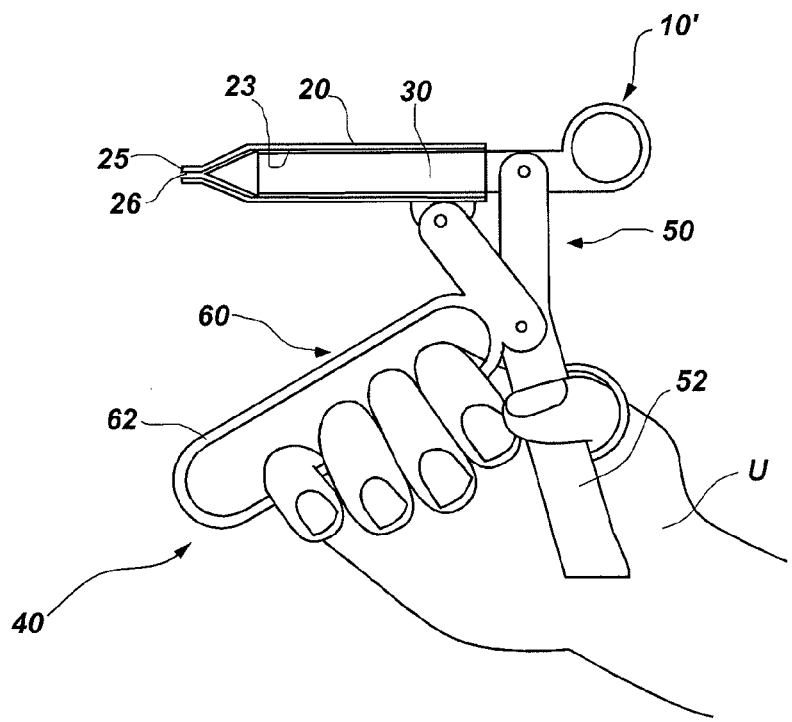
FIGS. 8A and 8B are schematic representations of use of an aspiration apparatus incorporating teachings of the present invention.
Figure 8B:
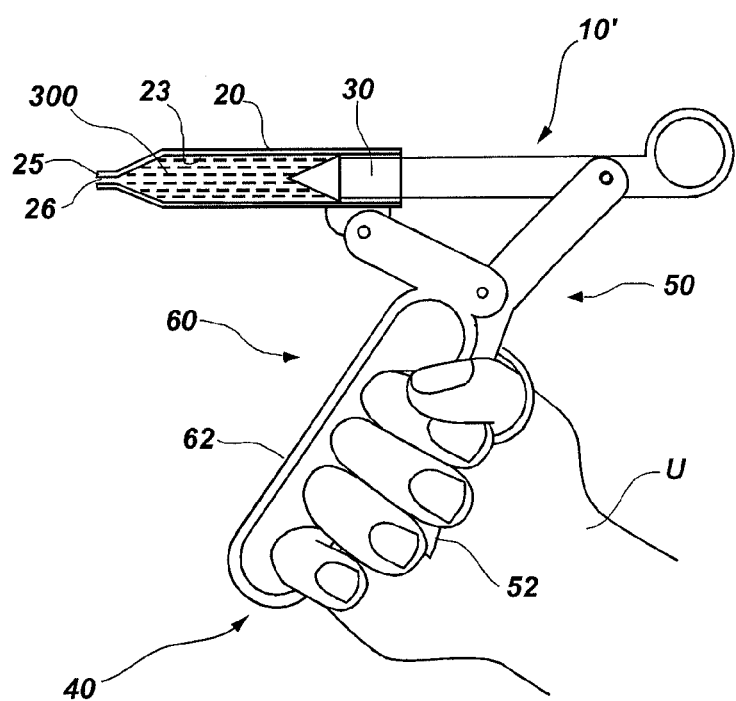

Turning now to FIGS. 8A and 8B, an example of the use of an aspiration apparatus incorporating teachings of the present invention is illustrated.

FIG. 8A illustrates an aspiration apparatus 10' in an initial position, in which a plunger 30 of a syringe is fully or almost fully disposed within receptacle 23 of barrel 20 and gripping ends 52 and 62 of second and first members 50 and 60 of handle 40 are positioned part apart from one another.

As a user U squeezes gripping ends 52 and 62 of second and first members 50 and 60 of handle 40 together, as shown in FIG. 8B, plunger 30 is drawn distally through receptacle 23 of barrel 20, creating a vacuum therein that, in turn, draws fluid 300, tissues, or cells through either lumen 26 of syringe tip 25 (FIGS. 1 and 2) or lumen 82 of aspiration port 80 (FIG. 3) and into receptacle 23.

Fluid 300 may then be removed from receptacle 23 of barrel 20 by moving gripping ends 52 and 62 of second and first members 50 and 60 of handle 40 apart from one another.

Returning reference to FIG. 1, handle 40 provides sufficient leverage that the force applied by a single hand of a user will be translated into an adequate amount of force upon plunger 30 and within receptacle 23 to force even relatively high viscosity fluids into receptacle 23. Moreover, the configurations of second and first members 50 and 60 of handle 40 facilitate gripping thereof with a single hand, the fine motor skills of which can be used in such a way as to precisely control the amount of fluid being introduced into or discharged from receptacle 23 of syringe barrel 20.

Aspiration apparatus incorporating teachings of the present invention may be used in a variety of different procedures, including, without limitation, obtaining samples of bodily fluids (e.g., blood, blood clots, etc.) and cells or tissues (e.g., with a biopsy needle or other biopsy instrument).

Although the foregoing description contains many specifics, these should not be construed as limiting the scope of the present invention, but merely as providing illustrations of some exemplary embodiments. Similarly, other embodiments of the invention may be devised which do not depart from the spirit or scope of the present invention. Features from different embodiments may be employed in combination. The scope of the invention is, therefore, indicated and limited only by the appended claims and their legal equivalents, rather than by the foregoing description. All additions, deletions, and modifications to the invention, as disclosed herein, which fall within the meaning and scope of the claims are to be embraced thereby.

What is claimed is:

1. A method for aspirating a sample, comprising:
    forcing proximal gripping ends of first and second handle members located on one side of a hinge toward one another to force distal connection ends of the first and second handle members on an opposite side of the hinge apart from one another, a distal connection end of the first handle member pivoting relative to a barrel of a syringe and supporting the barrel as the distal connection end of the second handle member is forced away from the distal connection end of the first handle member and draws a plunger of the syringe proximally out of the barrel.

2. The method of claim 1, further comprising:
    forming a vacuum within the barrel of the syringe as the plunger of the syringe is drawn proximally out of the barrel.

3. The method of claim 2, wherein the vacuum within the barrel draws a sample into the barrel.

4. The method of claim 3, further comprising:
    removing the sample from the barrel of the syringe.

5. The method of claim 4, wherein removing the sample comprises forcing the proximal gripping ends of the first and second handle members apart from one another to force the distal connection ends of the first and second handle members toward one another to force the plunger distally into the barrel of the syringe and to expel the sample from the syringe.

6. The method of claim 1, further comprising:
securing a sampling device to a distal end of the barrel of the syringe.

7. The method of claim 6, wherein securing the sampling device comprises securing at least one of a needle and a catheter to the distal end of the barrel of the syringe.

8. The method of claim 6, further comprising:
forming a vacuum within the barrel of the syringe and within the sampling device as the plunger of the syringe is drawn proximally out of the barrel.

9. The method of claim 8, wherein the vacuum draws a sample through the sampling device and into the barrel of the syringe.

10. The method of claim 9, further comprising:
removing the sampling device from the distal end of the barrel of the syringe.

11. The method of claim 9, further comprising:
removing the sample from the barrel of the syringe.

12. A method for aspirating a sample, comprising:
introducing a withdrawal element into communication with a desired location of a subject's body;
coupling the withdrawal element to a barrel of an aspiration apparatus in communication with the withdrawal element; and
generating a vacuum within the barrel by pivoting gripping portions of members of a handle of the aspiration apparatus together to move connection portions of members of the handles apart, causing a plunger of the aspiration apparatus, which is pivotally connected to a connection portion of one member of the handle, to move proximally through the barrel, which is pivotally connected to a connection portion of another member of the handle.

13. The method of claim 12, wherein:
introducing the withdrawal element comprises introducing a catheter into communication with a desired location of a subject's body; and
coupling the withdrawal element comprises coupling the catheter to the barrel of the aspiration apparatus.

14. The method of claim 12, wherein coupling is effected after introducing the withdrawal element into communication with the desired location of the subject's body.

15. The method of claim 12, wherein generating the vacuum comprises drawing a sample into the syringe.

16. The method of claim 15, further comprising:
expelling the sample from the syringe by moving the portions of the members of the handle away from one another to move the plunger distally through the barrel.

17. A method for aspirating a sample, comprising:
introducing a withdrawal element into communication with a desired location of a subject's body;
establishing flow communication between the withdrawal element and a barrel of an aspiration apparatus in communication with the withdrawal element; and
generating a vacuum within the barrel by pivoting gripping portions of members of a handle of the aspiration apparatus together to move connection portions of members of the handles apart, causing a plunger of the aspiration apparatus, which is pivotally connected to a connection portion of one member of the handle, to move proximally through the barrel, which is pivotally connected to a connection portion of another member of the handle.

18. The method of claim 17, wherein:
introducing the withdrawal element comprises introducing a catheter into communication with a desired location of a subject's body; and
establishing flow communication comprises establishing flow communication between the catheter and the barrel of the aspiration apparatus.

19. The method of claim 17, wherein, while pivoting gripping portions of the members of the handle of the aspiration apparatus together, a connection portion of a first member of the handle pivots relative to and supports the barrel as a connection portion of the second member draws the plunger out of the barrel.

20. The method of claim 17, wherein generating the vacuum comprises drawing a sample into the syringe.

21. The method of claim 20, further comprising:
expelling the sample from the syringe by moving the portions of the members of the handle away from one another to move the plunger distally through the barrel.

* * * * *